(12) United States Patent
Chen (10) Patent No.: US 9,986,792 B2
(45) Date of Patent: Jun. 5, 2018

(54) SNAP BUTTON AND PHYSIOLOGICAL SIGNAL DETECTING BELT THEREOF FOR IMPROVING ELECTRIC CONDUCTIVITY

(71) Applicant: ZENTAN TECHNOLOGY CO., LTD., New Taipei (TW)

(72) Inventor: Tong-Pie Chen, New Taipei (TW)

(73) Assignee: ZENTAN TECHNOLOGY CO., LTD., New Taipei (TW)

( * ) Notice: Subject to any disclaimer, the term of this patent is extended or adjusted under 35 U.S.C. 154(b) by 391 days.

(21) Appl. No.: 14/722,024

(22) Filed: May 26, 2015

(65) Prior Publication Data
US 2016/0270487 A1    Sep. 22, 2016

(30) Foreign Application Priority Data

Mar. 20, 2015   (TW) .............................. 104204208 U (51) Int. Cl.
*A61B 5/00*     (2006.01)
*A44B 17/00*   (2006.01)

(52) U.S. Cl.
CPC ........ *A44B 17/0023* (2013.01); *A44B 17/007* (2013.01); *A44B 17/0041* (2013.01); *A44B 17/0076* (2013.01); *A61B 5/6831* (2013.01); *A61B 5/6802* (2013.01); *A61B 5/6838* (2013.01); *A61B 2562/0209* (2013.01); *A61B 2562/18* (2013.01); *A61B 2562/225* (2013.01)

(58) Field of Classification Search
CPC ................ A61B 5/6831; A61B 5/6868; A61B 2562/225; A44B 17/0023; A44B 17/0041; A44B 17/007; A44B 17/0076
See application file for complete search history.

(56) References Cited

U.S. PATENT DOCUMENTS

| | | | | |
|---|---|---|---|---|
| 2002/0029444 A1* | 3/2002 | Lyle | ................... | A44B 17/0029 24/621 |
| 2015/0157265 A1* | 6/2015 | Kang | ................... | A61B 5/6831 600/394 |

\* cited by examiner

*Primary Examiner* — Tammie K Heller
(74) *Attorney, Agent, or Firm* — Li & Cai Intellectual Property (USA) Office (57) ABSTRACT

A snap button includes a male retaining member and a female retaining member. The male retaining member includes a base, a hollow cylinder, and at least one protrusion portion. The hollow cylinder is disposed on the base, the at least one protrusion portion is disposed on the base and at a periphery of the hollow cylinder. The female retaining member includes a main body which has a hollow tube body. The hollow cylinder is housed through the hollow tube body.

8 Claims, 8 Drawing Sheets

SNAP BUTTON AND PHYSIOLOGICAL SIGNAL DETECTING BELT THEREOF FOR IMPROVING ELECTRIC CONDUCTIVITY

BACKGROUND

1. Technical Field

The present disclosure relates to a snap button, in particular, to a snap button and a physiological signal detecting belt thereof for improving electric conductivity.

2. Description of Related Art

A snap button on the market is generally used to dispose the fabric between its male and female retaining members, and the male and female retaining members are united by mechanical stamping or other methods so that the fabric can be compressed between the male and female retaining members. However, the fabric is still loose and cannot be held tightly by the male and female retaining members.

As technology advances, conventional medical devices used in measuring various human physiological signals have been designed smaller and wireless so as to let people or patients measure their own physiological signals anytime and anywhere, not only for diseases that may be effectively controlled but also to decrease the frequency of seeing the doctor or accident events. Furthermore, this can be used for determining athletes' physiological status when they are training.

There are some physiological sensing belts on the market, that are surroundingly bundled on a human's chest to detect the physiological signals via a conductive fiber on the inner surface of the belt making contact with human's skin, and the physiological signals would be read, analyzed, and displayed by the snap button disposed on the conductive fiber and a signal transceiver fastened to each other to wirelessly transmit the signals to an external electronic device.

However, the detected physiological signals are highly connected with the electrical connectivity among the snap button, conductive fiber, and signal transceiver. If there is poor electrical contact between the snap button and the conductive fiber, it is liable to receive inaccurate and noisy physiological signals. Meanwhile, a contacted surface between the snap button and the conductive fiber is easily oxidized by sweat, causing problems such as inaccuracy and lots of noise in the signals.

Hence, it is important to overcome the abovementioned drawbacks in the art, to provide a snap button which can improve the results detected by the physiological signal detecting belt device and improve the accuracy of the physiological signal detected by the physiological signal detecting belt.

SUMMARY

An exemplary embodiment of the present disclosure provides a snap button and a physiological signal detecting belt with the snap button which can improve electric conductivity via at least one protrusion portion of the snap button piercing into a fabric or conductive fiber to increase the connectivity between the snap button and the fabric or conductive fiber.

To achieve the aforementioned purposes, one exemplary embodiment of the present disclosure is to provide a snap button which comprises a male retaining member and a female retaining member. The male retaining member includes a base, a hollow cylinder, and at least one protrusion portion, wherein the hollow cylinder is disposed on the base, the at least one protrusion portion is disposed on the base and at a periphery of the hollow cylinder. The female retaining member includes a main body which has a hollow tube body, wherein the hollow cylinder is housed through the hollow tube body.

Another exemplary embodiment of the present disclosure is to provide a physiological signal detecting belt with a snap button which comprises a male retaining member, a female retaining member, and an electrode member. The male retaining member includes a base, a hollow cylinder, and at least one protrusion portion, wherein the hollow cylinder is disposed on the base, the at least one protrusion portion is disposed on the base and at a periphery of the hollow cylinder. The female retaining member includes a main body having a hollow tube body, wherein the hollow cylinder is housed through the hollow tube body. The electrode member is disposed between the male and female retaining members, wherein the at least one protrusion portion pierces into the electrode member.

The advantage of the present disclosure is to provide a snap button and a physiological signal detecting belt with the snap button, that can increase the connectivity and the electric conductivity via the at least one protrusion portion disposed on the male retaining member which pierces into the fabric or electrode member so as to provide accurate physiological signals. In other words, the at least one protrusion portion of the snap button and the physiological signal detecting belt with the snap button of the present disclosure can be prevented from oxidation and can further avoid receiving inaccurate and noisy physiological signals by piercing into the fabric or electrode member.

In order to further understand the techniques, means and effects of the present disclosure, the following detailed descriptions and appended drawings are hereby referred to, such that, and through which, the purposes, features and aspects of the present disclosure can be thoroughly and concretely appreciated; however, the appended drawings are merely provided for reference and illustration, without any intention to be used for limiting the present disclosure.

BRIEF DESCRIPTION OF THE DRAWINGS

The accompanying drawings are included to provide a further understanding of the present disclosure, and are incorporated in and constitute a part of this specification. The drawings illustrate exemplary embodiments of the present disclosure and, together with the description, serve to explain the principles of the present disclosure.

DESCRIPTION OF THE EXEMPLARY EMBODIMENTS

Reference will now be made in detail to the exemplary embodiments of the present disclosure, examples of which are illustrated in the accompanying drawings. Wherever possible, the same reference numbers are used in the drawings and the description to refer to the same or like parts.

Figure 1:
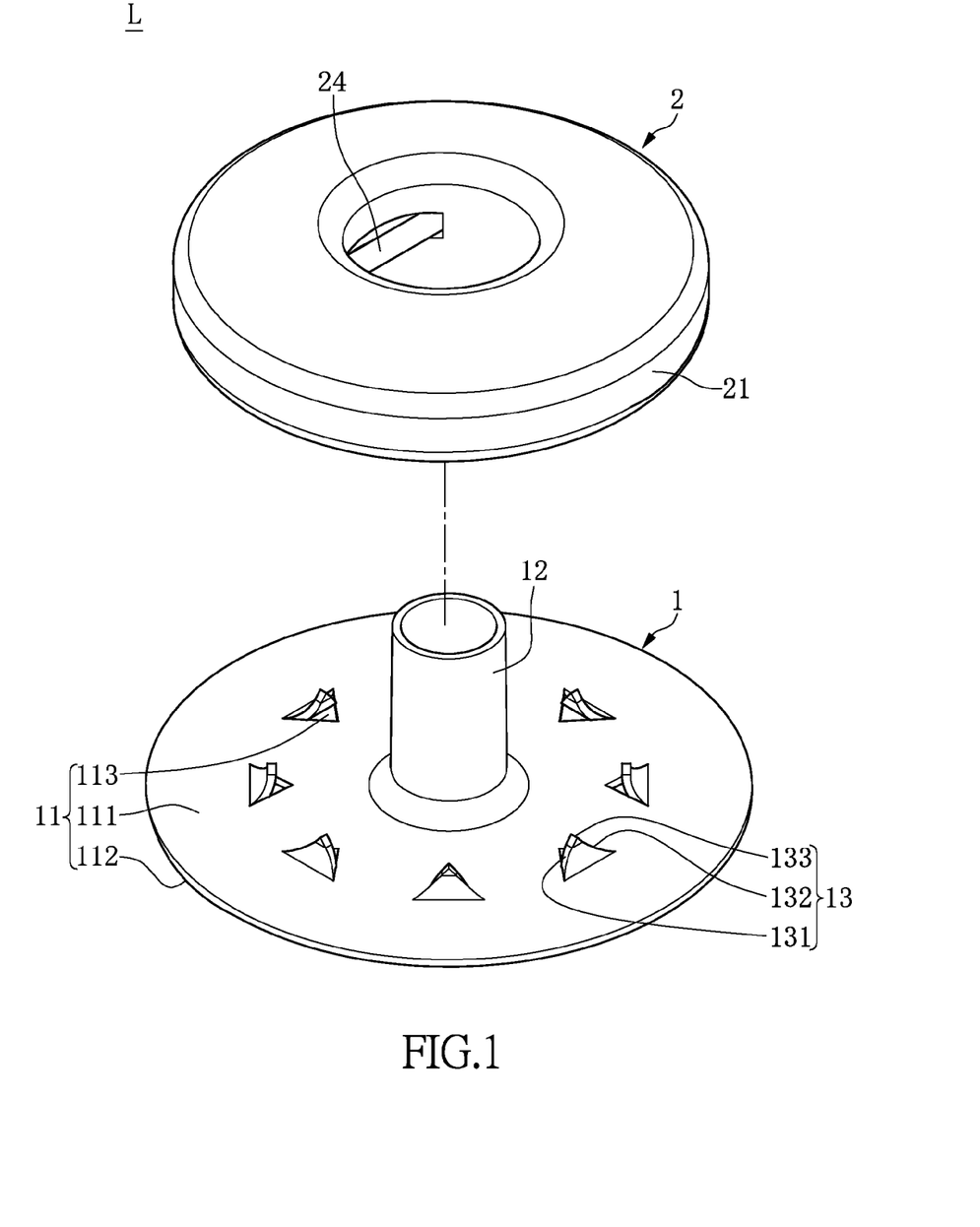
FIG. 1 shows one perspective of the schematic perspective diagram of one embodiment of the present disclosure.
Figure 2:
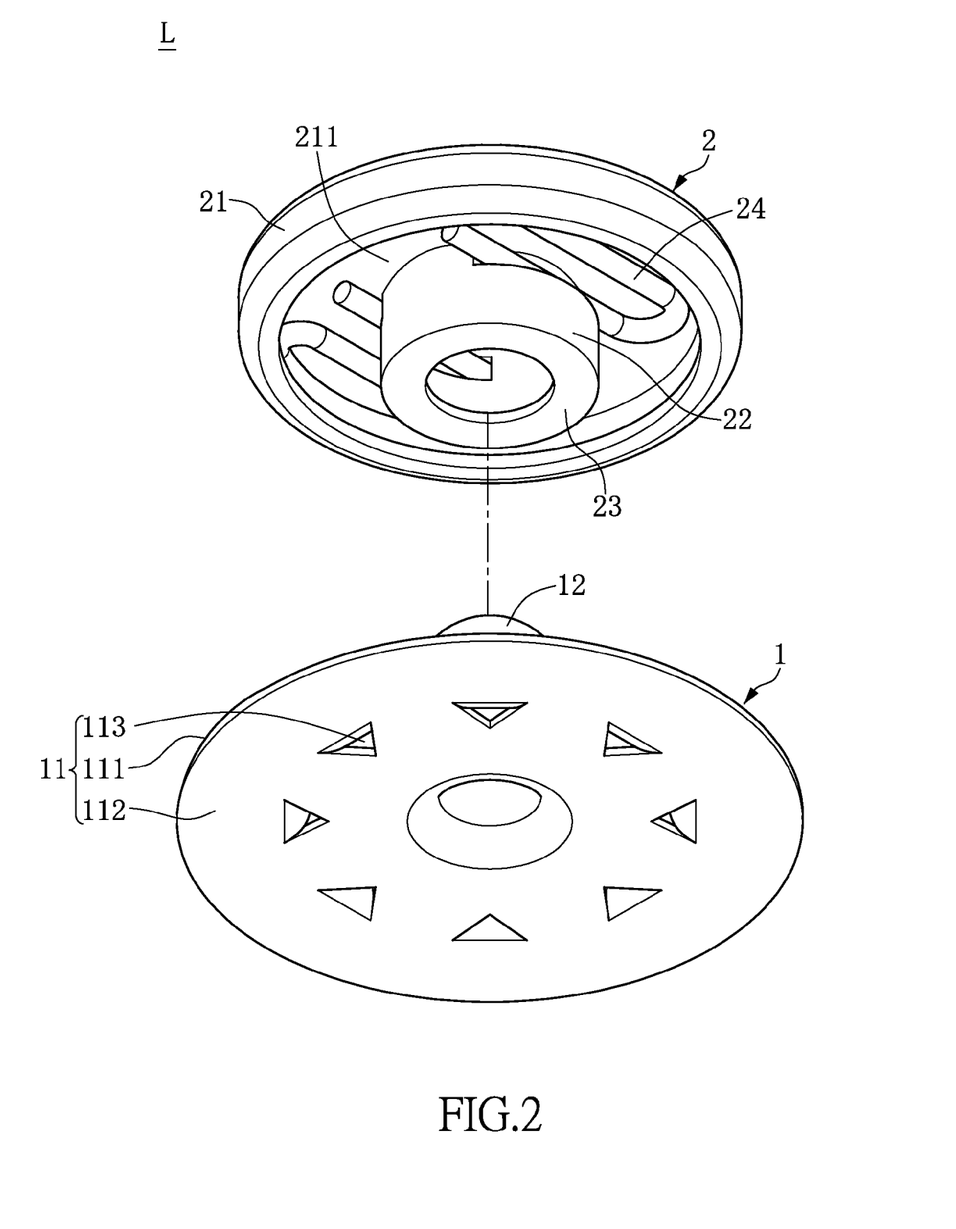
FIG. 2 shows another perspective of the schematic perspective diagram of the embodiment of the present disclosure.
Figure 3:
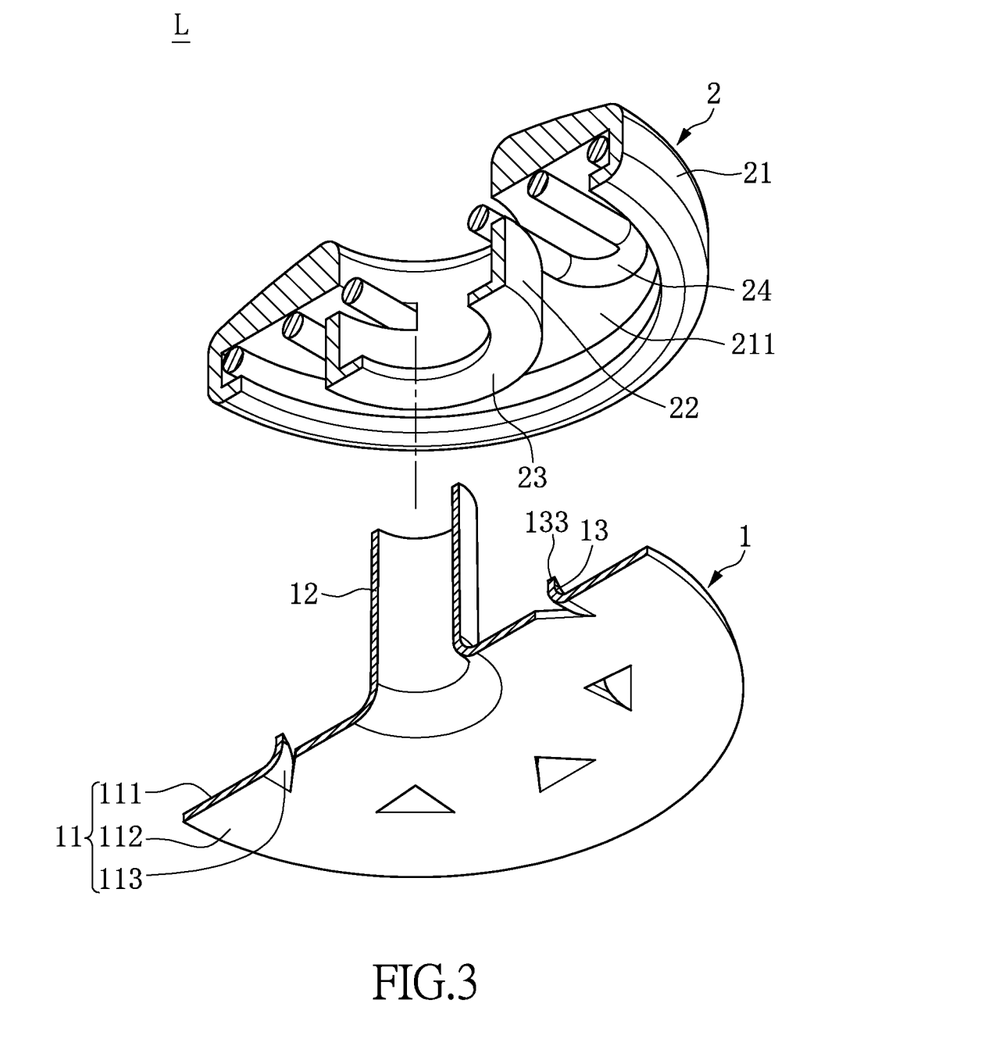
FIG. 3 shows a cross-sectional schematic perspective view of the embodiment of the present disclosure.
Figure 4:
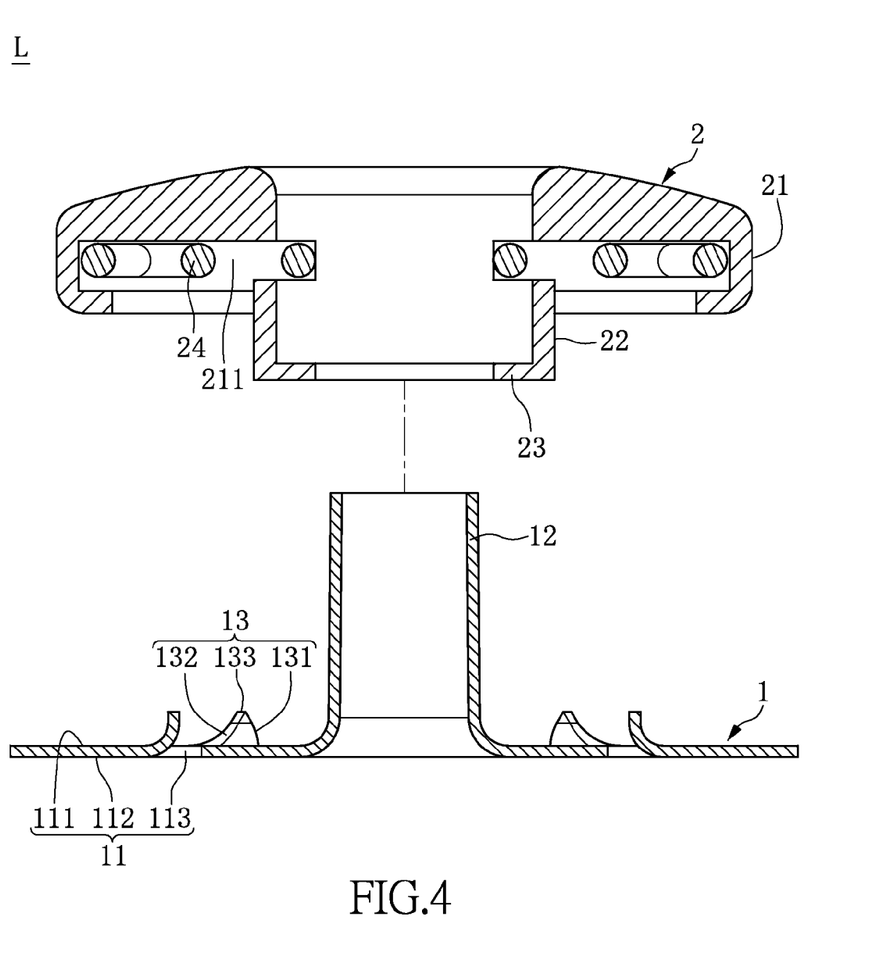
FIG. 4 is an exploded cross-sectional view of the embodiment of the present disclosure.

Relating to a first exemplary embodiment of the present disclosure, please refer to FIGS. 1 to 4. FIG. 1 shows one perspective of the schematic perspective diagram of one embodiment of the present disclosure, FIG. 2 shows another perspective of the schematic perspective diagram of the embodiment of the present disclosure, FIG. 3 shows a cross-sectional schematic perspective view of the embodiment of the present disclosure, and FIG. 4 is an exploded cross-sectional view of the embodiment of the present disclosure. The first embodiment of the present disclosure provides a snap button L including a male retaining member 1 and a female retaining member 2, for example, the snap button L of the present disclosure is modified from a conventional snap button. The male retaining member 1 includes a base 11, a hollow cylinder 12, and at least one protrusion portion 13. The hollow cylinder 12 is disposed on the base 11, the at least one protrusion portion 13 is disposed on the base 11 and at a periphery of the hollow cylinder 12. FIGS. 1 to 3 show that, in the present disclosure, the at least one protrusion portion 13 may be a plurality, and the plurality of protrusion portions 13 may be surroundingly disposed at the periphery of the hollow cylinder 12. Specifically, in the embodiment of the present disclosure, the base 11 has a first surface 111 and a second surface 112, the first and second surfaces 111, 112 are disposed on the opposite sides of the base 11 respectively, and the hollow cylinder 12 and the at least one protrusion portion 13 are both disposed on the first surface 111. For example, the base 11, hollow cylinder 12, and at least one protrusion portion 13 can be made from an identical material.

A shown in FIGS. 1 to 4, the at least one protrusion portion 13 of the male retaining member 1 is part of the base 11, and the at least one protrusion portion 13 is bent and extended from the second surface 112 toward the first surface 111 and is protruded out of the first surface 111. For instance, in the embodiment of the present disclosure, the at least one protrusion portion 13 can be formed via mechanical stamping, and the steps are as follows: a) an end portion of the base 11 is cut with a piece of valve; b) the valve is thrust from the second surface 112 toward the first surface 111 to form the at least one protrusion portion 13 and at least one through hole 113, but the present disclosure is not limited thereto, such as, the at least one protrusion portion 13 can be formed on the first surface 111 of the base 11 via other ways. Moreover, in the embodiment of the present disclosure, since the at least one through hole 113 is formed by the at least one protrusion portion 13, the least one through hole 113 has the identical shape with the at least one protrusion portion 13. In other words, the at least one protrusion portion 13 is extended along one side of the at least one through hole 113 toward the first surface 111.

In the embodiment of the present disclosure, the at least one protrusion portion 13 has a first side 131 and a second side 132, and the first side 131 and the second side 132 intersect each other at an endpoint 133, wherein the endpoint 133 formed by the first side 131 and the second side 132 of the at least one protrusion portion 13 has a sharp tip which can pierce a fiber, a fabric, and a conductive rubber. Preferably, the at least one protrusion portion 13 is a triangle, and the endpoint 133 intersected with the first side 131 and the second side 132 is an acute angle so as to perforate or pierce the materials such as a fiber, a fabric, and a conductive rubber. However, the endpoint 133 does not have to be exactly the same as the aspects shown in FIGS. 1 to 3, as long as the endpoint 133 has the sharp tip which can pierce a fiber, a fabric, or a conductive rubber, and it is within the scope of the present disclosure.

According to the above, the male retaining member 1 can be cooperatively disposed with the female retaining member 2, in particularly, the female retaining member 2 includes a main body 21 which has a hollow tube body 22, and the hollow cylinder 12 of the male retaining member 1 is housed through the hollow tube body 22 of the female retaining member 2. The female retaining member 2 further comprises an elastic component 24, and the main body 21 of the female retaining member 2 is formed with an accommodating space 211, wherein the accommodating space 211 is disposed on and surrounded at a periphery of the hollow tube body 22, and the elastic component 24 is disposed in the accommodating space 211 of the female retaining member 2.

The female retaining member 2 further comprises an end part 23 disposed at one end of the hollow tube body 22 to enclose a part of the hollow tube body 22. In this way, when the male and female retaining members 1, 2 cooperate with a fabric or a fiber, the hollow cylinder 12 of the male retaining member 1 is housed through the hollow tube body 22 of the female retaining member 2, the at least one protrusion portion 13 disposed at the male retaining member 1 pierces through or into the fabric or fiber, and the end part 23 of the female retaining member 2 withstands against the fabric or fiber so as to increase a binding force between the male and female retaining members 1, 2 and the fabric or fiber.

The first embodiment of the present disclosure provides the snap button L which has a better binding force between the male and female retaining members 1, 2 and the fabric or fiber by the at least one protrusion portion 13 disposed at the male retaining member 1 piercing into the fabric or fiber.

Figure 5:
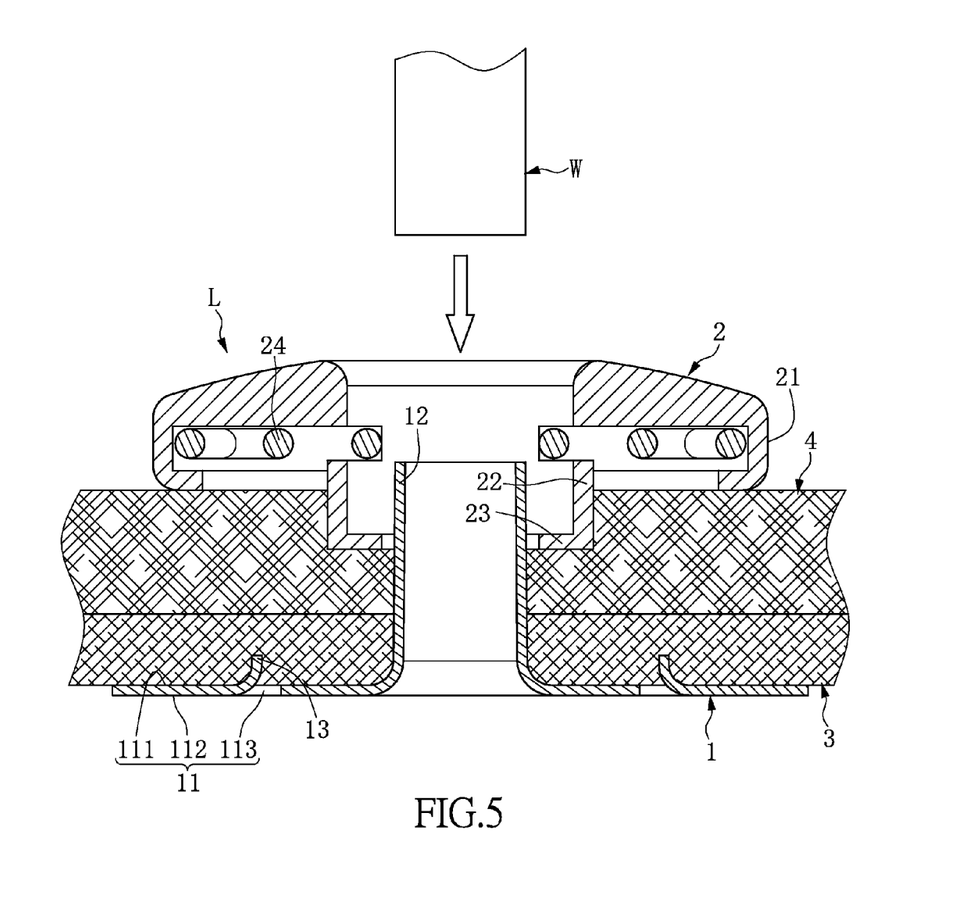
FIG. 5 shows an assembled cross-sectional view of a second embodiment of the present disclosure.
Figure 6:
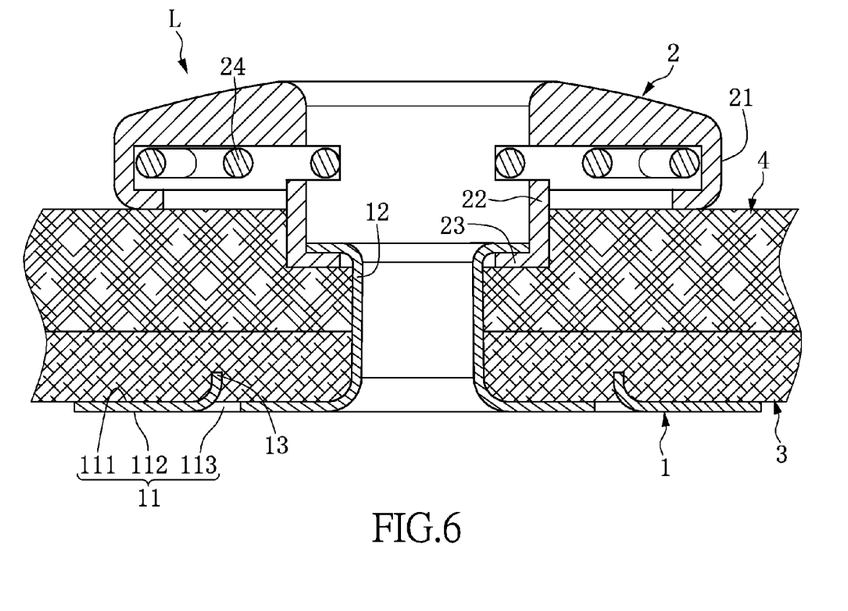
FIG. 6 shows another assembled cross-sectional view of the second embodiment of the present disclosure.

FIG. 5 shows an assembled cross-sectional view of a second embodiment of the present disclosure, and FIG. 6 shows another assembled cross-sectional view of the second embodiment of the present disclosure. The second embodiment of the present disclosure provides a physiological signal detecting belt S with the snap button L which can improve electric conductivity. The physiological signal detecting belt S with the snap button L comprises a male retaining member 1, a female retaining member 2, and an electrode member 3, for example, in the second embodiment of the present disclosure, the electrode member 3 can be a cloth or colloid having electric conductivity such as a conductive fiber, conductive fabric, conductive rubber, or multilayer composite material.

Then, as described in the abovementioned first embodiment, the male retaining member 1 includes a base 11, a hollow cylinder 12, and at least one protrusion portion 13. The hollow cylinder 12 is disposed on the base 11, and the at least one protrusion portion 13 is disposed on the base 11 and at a periphery of the hollow cylinder 12. The base 11 has a first surface 111 and a second surface 112, the first and second surfaces 111, 112 are disposed on the opposite sites of the base 11 respectively, and the hollow cylinder 12 and the at least one protrusion portion 13 are both disposed on the first surface 111. The at least one protrusion portion 13 of the male retaining member 1 is part of the base 11, and the at least one protrusion portion 13 is bent and extended from the second surface 112 toward the first surface 111 and is protruded out of the first surface 111. In this case, the at least one protrusion portion 13 has a first side 131 and a second side 132, and the first side 131 and the second side 132 intersect each other at an endpoint 133, wherein the endpoint 133 formed by the first side 131 and the second side 132 of the at least one protrusion portion 13 has a sharp tip which can pierce the electrode member 3. The female retaining member 2 includes a main body 21 which has a hollow tube body 22, and the hollow cylinder 12 of the male retaining member 1 is housed through the hollow tube body 22 of the female retaining member 2. The female retaining member 2 further comprises an elastic component 24, and the main body 21 of the female retaining member 2 is formed with an accommodating space 211, wherein the accommodating space 211 is disposed on and surrounded at a periphery of the hollow tube body 22, and the elastic component 24 is disposed in the accommodating space 211 of the female retaining member 2. The female retaining member 2 further comprises an end part 23 disposed at one end of the hollow tube body 22 to enclose a part of the hollow tube body 22.

The electrode member 3 is disposed between the male and female retaining members 1, 2, wherein the at least one protrusion portion 13 pierces into the electrode member 3. In the embodiment of the present disclosure, the electrode member 3 has electric conductivity, the at least one protrusion portion 13 pierces into the electrode member 3, so that the electrical connectivity between the electrode member 3 and the male retaining member 1 can be better and more stable, but the present disclosure is not limited thereto. The structures of the male and female retaining members 1, 2 of the second embodiment of the present disclosure are identical to that of the abovementioned first embodiment, thus they are not described again herein.

Furthermore, as shown in FIGS. 5 and 6, the physiological signal detecting belt S with the snap button L of the second embodiment of the present disclosure further comprises a belt member 4, wherein the electrode member 3 is disposed on one surface of the belt member 4, and the electrode member 3 and the belt member 4 both are disposed between the male and female retaining members 1, 2. By this way, the first surface 111 on the base 11 of the male retaining member 1 is connected to the electrode member 3, the electrode member 3 is then bound to the belt member 4 using the molding methods such as hot pressing, coating, spinning and weaving, textile printing, or sewing, and one surface of the end part 23 of the female retaining member 2 is abutted adjacently to the belt member 4. The belt member 4 can be fabricated from, but is not limited to natural fibers, artificial fibers, and combinations thereof. Examples of the natural fibers include, but are not limited to cotton, hemp, silk, and wool. Examples of the artificial fibers include, but are not limited to rayon fibers, nylon fibers, polyester fibers or acrylic fibers. The fabric can be any knitting patterns, e.g., flat-woven, non-woven, mesh-woven, or knitted fabric.

When the male retaining member 1, electrode member 3, belt member 4, and female retaining member 2 are stacked in sequence and the hollow cylinder 12 of the male retaining member 1 is housed through the hollow tube body 22 of the female retaining member 2, a stamping device W applies a pressure to the hollow cylinder 12 of the male retaining member 1. A part of the hollow cylinder 12 is then bended or deformed, and the bended part of the hollow cylinder 12 is abutted against another surface of the end part 23 of the female retaining member 2, such that the two surfaces of the end part 23 are gripped by the belt member 4 and the part of the hollow cylinder 12. After that, the male retaining member 1, electrode member 3, and female retaining member 2 can be electrically connected to each other. Nevertheless, the figures of the embodiment of the present disclosure show that, the hollow cylinder 12 having an outside diameter is smaller than the end part 23 having an inside diameter, but in other embodiments, the hollow cylinder 12 having an outside diameter may be larger than the end part 23 having an inside diameter. By applying a pressure to the hollow cylinder 12 using the stamping device W, the hollow cylinder 12 is deformed so as to bind the male and female retaining members 1, 2 together. Though the figures of the embodiment of the present disclosure show that the hollow cylinder 12 has a plane which is vertical to a horizontal line, in other embodiments the hollow cylinder 12 may have taper shape, and the outside diameter of the top of the hollow cylinder 12 is smaller than the inside diameter of the end part 23. When the hollow cylinder 12 extends toward to the base 11, the outside diameter of the hollow cylinder 12 is gradually increased to be larger than the inside diameter of the end part 23. Therefore, the top of the hollow cylinder 12 can easily pass through the hollow tube body formed from the end part 23, and a pressure can be applied to the end portion of the hollow cylinder 12, being larger than the inside diameter of the end part 23, to deform the hollow cylinder 12 so as to bind the male and female retaining members together.

In addition, referring to FIGS. 5 and 6, the at least one protrusion portion 13 can pierce into the electrode member 3 but not pierce through it. In other embodiments, the at least one protrusion portion 13 can pierce through the electrode member 3 and even into the belt member 4, but the present disclosure is not limited thereto. The at least one protrusion portion 13 pierces into and is covered by the electrode member 3, and the at least one protrusion portion 13 can be protected from oxidation. The at least one protrusion portion 13 and the first surface 111 has a bending angle ranging from 30 to 90 degrees, but the present disclosure is not limited thereto. As long as the at least one protrusion portion 13 can pierce into the electrode member 3, the electrode member 3 and the snap button L can be firmly bound together.

Figure 7:
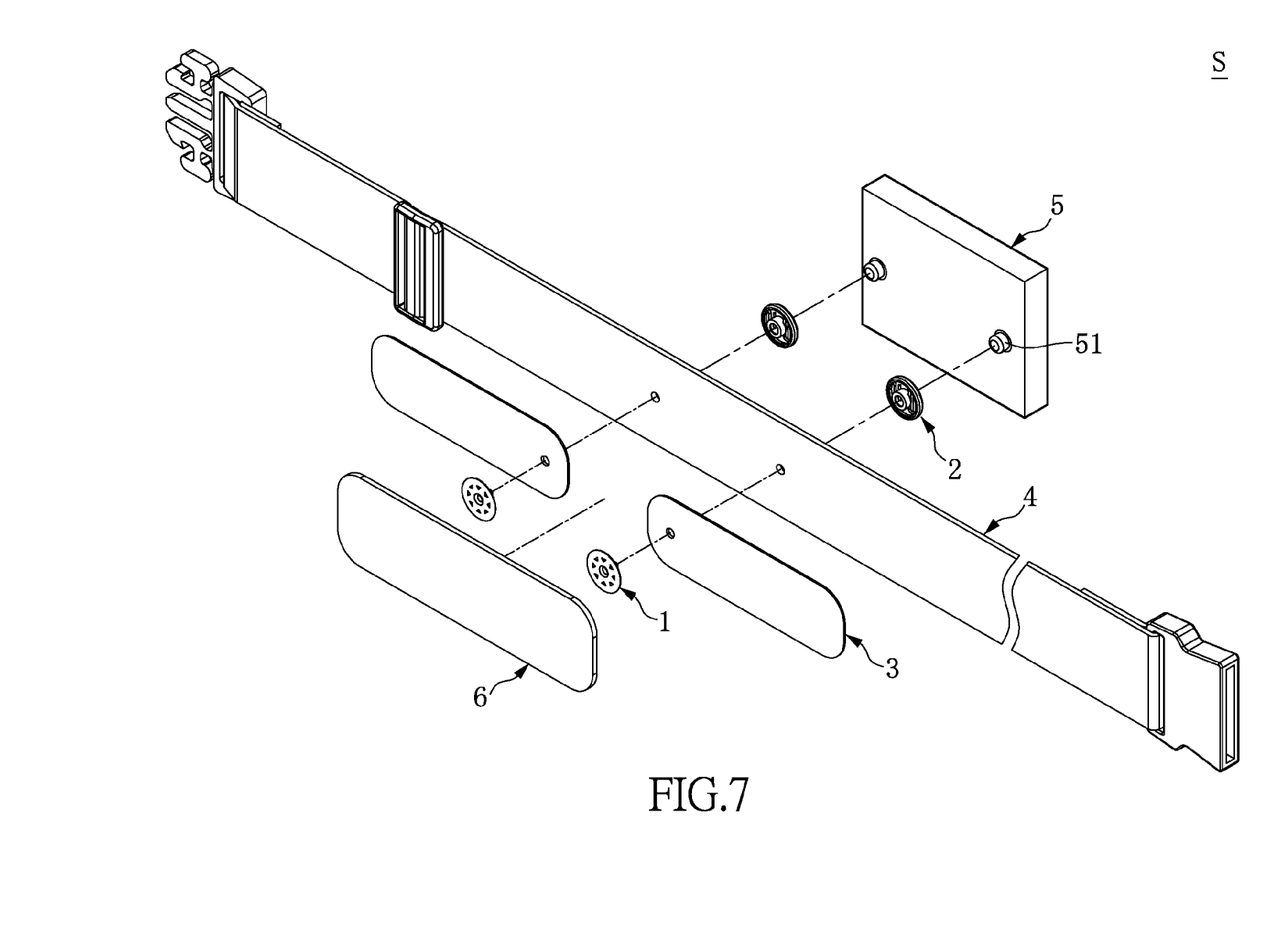
FIG. 7 is an exploded view of the second embodiment of the present disclosure being in use.
Figure 8:
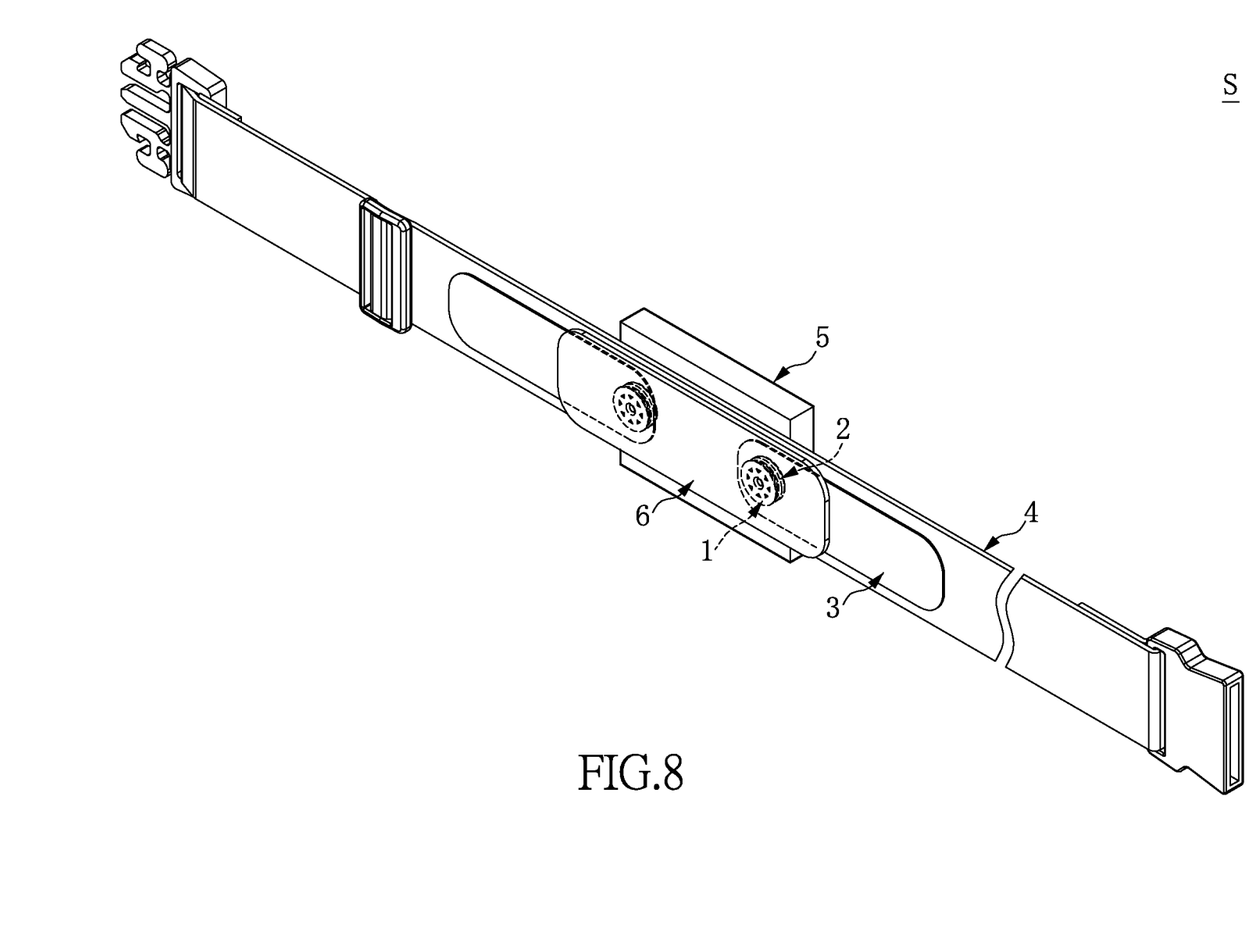
FIG. 8 is an assembled view of the second embodiment of the present disclosure being in use.

According to FIGS. 7 and 8, FIG. 7 is an exploded view of the second embodiment of the present disclosure being in use, and FIG. 8 is an assembled view of the second embodiment of the present disclosure being in use. A physiological signal detecting belt S with a snap button L of the second embodiment of the present disclosure can be cooperatively used with a signal transceiver 5 and an isolator 6.

The signal transceiver 5 includes a signal transmitting terminal 51 corresponding to the main body 21 of the female retaining member 2. The signal transmitting terminal 51 can be fastened by the elastic component 24 disposed in the accommodating space 211 of the female retaining member 2. In other words, while the signal transmitting terminal 51 is fastened in the main body 21 of the female retaining member 2, the signal transmitting terminal 51 will be held by the elastic component 24 and will abut against the main body 21 so as to electrically connect with each other. Hence, the human's physiological signals can be transmitted to the signal transceiver 5 by electrically connecting the signal transmitting terminal 51 and the female retaining member 2, and the physiological signals can be read, analyzed, and displayed by transmitting the signals to an external electronic device (not shown) via the signal transceiver 5. Certainly, the product of the present disclosure can surround around the head, arms, and other parts of body to measure the physiological signals, such as electrocardiograms (ECG), electroencephalography (EEG), body temperature, and pulse.

To avoid the signal transceiver 5 being affected by sweat (water), the physiological signal detecting belt S of the second embodiment of the present disclosure further comprises an isolator 6 disposed between two snap buttons L, so as to isolate it from water. The isolator 6 covers parts of two electrode members 3 respectively, and covers the belt member 4 between the two electrode members 3 simultaneously. For example, the isolator 6 can be an insulating material. The isolator 6 can be bound to the belt member 4 using the binding methods, e.g., gluing, sewing, ultrasonic bonding, or hot laminating. Additionally, owing to the isolator 6 covers the male retaining member 1 of the snap button L, the isolator 6 can prevent the human skin directly contacting the male retaining member 1 to avoid the foreign-body sensation and it has a better look. The isolator 6 also can fix the snap button L and prevent the human body directly contacting the snap button L so that the signals transmitted from the snap button L to the signal transceiver 5 will not be affected.

The physiological signal detecting belt S with the snap button L of the second embodiment of the present disclosure has more stable electric conductivity using the at least one protrusion portion 13 disposed on the male retaining member 1 to pierce into or pierce through the electrode member 3, as to the electrical connectivity among the male retaining member 1, female retaining member 2, and electrode member 3. Meanwhile, since the at least one protrusion portion 13 pierces into or pierces through the electrode member 3, the snap button L and the electrode member 3 are not easily rotated and loosed, such that receiving inaccurate and noisy physiological signals can be avoided.

In summary, the advantage of the present disclosure is that the snap button L and the physiological signal detecting belt S with the snap button L of the embodiment of the present disclosure has better binding force and electric conductivity between the male retaining member 1 and the fabric or the electrode member 3 by using the at least one protrusion portion 13 disposed on the male retaining member 1 to pierce into the fabric or electrode member 3 so as to provide accurate physiological signals. It also can be the that the snap button L and the physiological signal detecting belt S with the snap button L of the embodiment of the present disclosure can prevent problems such as receiving inaccurate and noisy physiological signals by piercing into the fabric or the electrode member 3 so that the at least one protrusion portion 13 can be prevented from oxidization. At the same time, because the at least one protrusion portion 13 pierces into the fabric or electrode member 3, the snap button L and the fabric or electrode member 3 are not easily rotated and loosed.

The above-mentioned descriptions represent merely the exemplary embodiment of the present disclosure, without any intention to limit the scope of the present disclosure thereto. Various equivalent changes, alterations or modifications based on the claims of present disclosure are all consequently viewed as being embraced by the scope of the present disclosure.

What is claimed is:

1. A physiological signal detecting belt, comprising:
    a snap button including:
        a male retaining member including a base, a hollow cylinder, and a plurality of protrusion portions, wherein the base has a first surface and an opposite second surface, the base has a plurality of through holes penetrating the first surface to the second surface, the hollow cylinder is disposed on the first surface of the base, the protrusion portions are disposed at a periphery of the hollow cylinder, the protrusion portions are respectively corresponding in shape to the through holes, and each of the protrusion portions extends from an inner wall defining the corresponding through hole in a direction from the second surface to the first surface, wherein each of the protrusion portions includes a sharp tip having an acute angle; and
        a female retaining member including a main body having hollow tube body, wherein the hollow cylinder is housed through the hollow tube body, and the female retaining member and the male retaining member are electrically connected to each other;
    a belt member; and
    an electrode member having electric conductivity and disposed on one surface of the belt member, wherein the belt member and the electrode member are sandwiched between the male and female retaining members, wherein each of the protrusion portions pierces into the electrode member by using the sharp tip thereof so as to establish an electrical connection there-between, thereby enabling the first surface of the base to flatly contact the electrode member.

2. The physiological signal detecting belt according to claim 1, wherein each of the protrusion portions is entirely embedded in the electrode member.

3. The physiological signal detecting belt according to claim 1, further comprising: a signal transceiver including a signal transmitting terminal; wherein the signal transmitting terminal is fastened in the main body of the female retaining member, and the signal transmitting terminal is electrically connected to the electrode member through the snap button.

4. The physiological signal detecting belt according to claim 1, wherein each of the protrusion portions is a triangle sheet having a bending angle within a range of 30-90 degrees.

5. A physiological signal detecting belt, comprising:
    a snap button including:
        a male retaining member including a base, a hollow cylinder, and a protrusion portion, wherein the base has a first surface and an opposite second surface, the base has a through hole penetrating the first surface to the second surface, the hollow cylinder is disposed on the first surface of the base, the protrusion portion is disposed at a periphery of the hollow cylinder, the protrusion portion is corresponding in shape to the through hole, and the protrusion portion extends from an inner wall defining the through hole in a direction from the second surface to the first surface, wherein the protrusion portion includes a sharp tip having an acute angle; and
        a female retaining member housing the hollow cylinder, wherein the female retaining member and the male retaining member are electrically connected to each other;
    a belt member; and
    an electrode member having electric conductivity and disposed on one surface of the belt member, wherein the belt member and the electrode member are sandwiched between the male and female retaining members, wherein the protrusion portion pierces into the electrode member by using the sharp tip so as to establish an electrical connection there-between, thereby enabling the first surface of the base to flatly contact the electrode member.

6. The physiological signal detecting belt according to claim 5, wherein the protrusion portion is entirely embedded in the electrode member.

7. The physiological signal detecting belt according to claim 5, further comprising: a signal transceiver including a signal transmitting terminal; wherein the signal transmitting terminal is fastened in the female retaining member, and the signal transmitting terminal is electrically connected to the electrode member through the snap button.

8. The physiological signal detecting belt according to claim 5, wherein each of the protrusion portions is a triangle sheet having a bending angle within a range of 30-90 degrees.

\* \* \* \* \*